US012810521B2

(12) United States Patent
Flohr

(10) Patent No.: US 12,810,521 B2
(45) Date of Patent: Nov. 24, 2026

(54) METHOD AND DEVICE FOR RECONSTRUCTING VIRTUAL MONOENERGETIC IMAGES

(71) Applicant: Siemens Healthineers AG, Forchheim (DE)

(72) Inventor: Thomas Flohr, Uehlfeld (DE)

(73) Assignee: Siemens Healthineers AG, Forchheim (DE)

( * ) Notice: Subject to any disclaimer, the term of this patent is extended or adjusted under 35 U.S.C. 154(b) by 213 days.

(21) Appl. No.: 18/738,456

(22) Filed: Jun. 10, 2024

(65) Prior Publication Data

US 2024/0412441 A1 Dec. 12, 2024

(30) Foreign Application Priority Data

Jun. 12, 2023 (DE) ..................... 10 2023 205 410.8

(51) Int. Cl.

| | |
|---|---|
| ***G06T 15/00*** | (2011.01) |
| ***A61B 6/00*** | (2006.01) |
| ***A61B 6/03*** | (2006.01) |
| ***A61B 6/50*** | (2024.01) |
| ***G06T 7/00*** | (2017.01) |
| ***G06T 7/10*** | (2017.01) |

(52) U.S. Cl.

CPC .............. *G06T 15/00* (2013.01); *A61B 6/032* (2013.01); *A61B 6/504* (2013.01); *A61B 6/5205* (2013.01); *G06T 7/0014* (2013.01); *G06T 7/10* (2017.01); *G06T 2207/10081* (2013.01); *G06T 2207/30101* (2013.01); *G06T 2210/41* (2013.01)

(58) Field of Classification Search

CPC ......... G06T 15/00; G06T 7/0014; G06T 7/10; G06T 2207/10081; G06T 2207/30101; G06T 2210/41; G06T 12/00; G06T 12/10; G06T 2211/408; A61B 6/032; A61B 6/504; A61B 6/5205; A61B 6/481; A61B 6/482; A61B 6/507; A61B 6/52

See application file for complete search history.

(56) References Cited

U.S. PATENT DOCUMENTS

| | | | | |
|---|---|---|---|---|
| 2010/0310036 A1* | 12/2010 | Burleton | ................ | A61B 6/405 378/5 |
| 2012/0039440 A1* | 2/2012 | Fan | ........................ | A61B 6/482 378/62 |
| 2021/0110583 A1 | 4/2021 | Lee et al. | | |
| 2022/0270251 A1* | 8/2022 | Schmidt | ................. | A61B 6/482 |

FOREIGN PATENT DOCUMENTS

DE 102021201809 A1 8/2022

* cited by examiner

*Primary Examiner* — Daniel F Hajnik
*Assistant Examiner* — Chris Alejandro Puntier
(74) *Attorney, Agent, or Firm* — Harness, Dickey & Pierce, P.L.C.

(57) ABSTRACT

One or more example embodiments relates to a method for reconstructing virtual monoenergetic images comprising acquiring spectral CT data at at least two different average radiation energies; reconstructing virtual monoenergetic images (VMIs) from the CT data, a respective VMI energy of the VMIs varies along the patient longitudinal axis, a 3D image of at least a part of the patient being based on the VMIs; and outputting the virtual monoenergetic images. One or more example embodiments further relates to a corresponding device, as well as to a control facility and a CT system.

14 Claims, 2 Drawing Sheets

METHOD AND DEVICE FOR RECONSTRUCTING VIRTUAL MONOENERGETIC IMAGES

CROSS-REFERENCE TO RELATED APPLICATION(S)

The present application claims priority under 35 U.S.C. § 119 to German Patent Application No. 10 2023 205 410.8, filed Jun. 12, 2023, the entire contents of which is incorporated herein by reference.

FIELD

One or more example embodiments relates to a method and a device for reconstructing virtual monoenergetic images and such as a method for controlling a computed tomography system ("CT system").

RELATED ART

Spectral acquisition methods in the field of computed tomography (CT) have become a permanent component of examination practice in daily clinical routine. Owing to its unique postprocessing capabilities allowing for improved assessment of all regions of the body, dual-energy CT (DECT) or multi-energy CT has evolved into a routinely employed imaging modality. In addition to the reconstruction of polyenergetic images, the reconstruction of virtual monoenergetic images (VMIs) has advantages for contrast-free as well as for contrast-enhanced spectral CT acquisition methods.

Virtual monoenergetic images are spectral CT data acquisitions which are not based on any energy spectrum of the X-ray beam but which simulate a single (average) photon energy. This energy is generally in the region of a few tens of kiloelectron volts (keV). This energy, on which the reconstruction is based, is referred to in this publication as "VMI energy" in order to better differentiate it from other energies (for example the radiation energies). This VMI energy has little to do with the X-ray energies used for image acquisition, being rather a simulated energy or energy used for the reconstruction. A comparatively low VMI energy of 50 keV for example increases the contrast in the images and is therefore particularly attractive for contrast media applications.

Virtual monoenergetic images are often reconstructed in CT angiography procedures. When iodine is chosen as the contrast medium, these images, acquired at a VMI energy of 55 keV for example, increase the iodine contrast-to-noise ratio. The potential radiation dose or the concentration or volume of contrast medium can be reduced as a result.

Particularly in CT angiography scans, more especially of the lung, for example when pulmonary embolisms are suspected, a variation in the iodine contrast often results, in particular in the direction of the longitudinal axis of the patient (z-axis). In this case, in the shoulder area in the region of the subclavian vein, through which the inflow of contrast medium generally occurs, the iodine contrast is frequently so intensely increased that the images become difficult to diagnose as a result of this overbeaming. This represents a serious problem.

On the other hand, in a CT angiography (CTA) scan of the entire aorta or of the pelvic or leg vessels using non-optimal contrast medium protocols or scan protocols, a decrease in the contrast medium concentration toward the legs can result, which is not due to anatomical factors. This occurs for example when a scan is started too early or the feedforward rate is too high, and likewise represents a serious problem.

SUMMARY

Where significant differences in contrast occur within the scan volume, in particular along the patient longitudinal axis, it has previously been possible only to conduct additional reconstructions of the entire scan volume using VMIs using other VMI energies. For example, in the case of overbeaming in the shoulder region during a CTA scan of the lung, additional VMIs acquired at higher VMI energy (and consequently lower iodine contrast) can be calculated in addition to the normally reconstructed VMIs. With a reduction in contrast in the direction of the legs during a pelvis-leg CTA, additional VMIs acquired at lower VMI energy (and consequently higher iodine contrast) can be reconstructed. These VMIs may also be calculated only in parts of the scan volume, though this requires a manual definition of the respective region by the user. In any case, multiple image datasets are produced as a result of this approach and these must be subjected to diagnostic assessment alongside one another.

One or more example embodiments provides a more convenient alternative method and a corresponding device for reconstructing virtual monoenergetic images, such as for controlling a CT system, via which the above-described disadvantages are avoided.

This is achieved via a method according to claim 1, a device according to claim 10 and also via a control facility according to claim 11 and a CT system according to claim 12.

BRIEF DESCRIPTION OF THE DRAWINGS

The invention is explained in more detail below with the aid of exemplary embodiments and with reference to the attached figures. Like components in the different figures are in this case labeled with identical reference signs. The figures are generally not to scale. In the figures.

DETAILED DESCRIPTION

Figure 1:
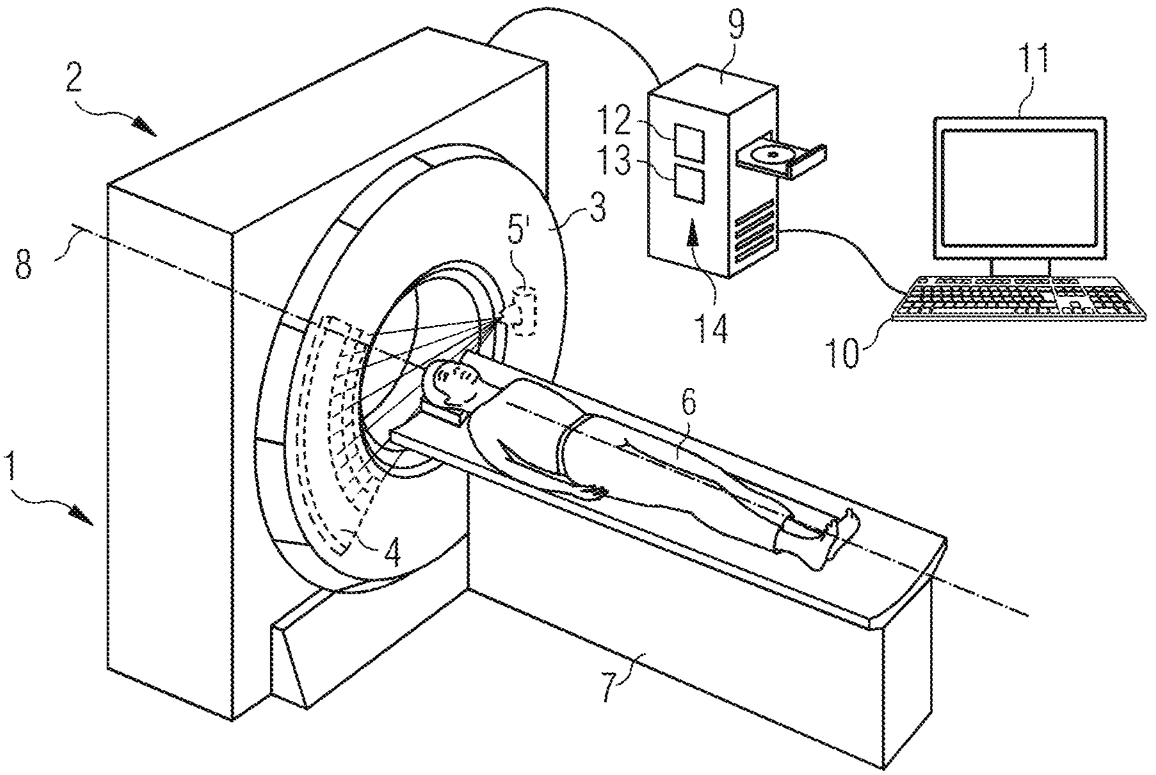
FIG. 1 shows a roughly schematic representation of a CT system comprising an exemplary embodiment of a control facility having a device for performing a method according to one or more example embodiments.

The method according to one or more example embodiments serves for reconstructing virtual monoenergetic images (VMIs). In particular, the method is embodied to be performed in a computed tomography system and then serves in principle for controlling said CT system. The method comprises the following steps:

- acquiring spectral CT data at at least two different radiation energies (i.e. in principle dual-energy CT or multi-energy CT),
- reconstructing virtual monoenergetic images from the CT data, the VMI energy of which images varies along the patient longitudinal axis and which together result in a 3D image of at least a part of the patient, for example in the form of an image stack, outputting the virtual monoenergetic images.

The acquisition of spectral CT data is generally known in the prior art and is preferably carried out within the scope of a CT angiography scan. It is particularly preferred for a contrast medium, for example iodine, to have been administered to the patient prior to the acquisition. The acquisition is then performed while the patient carries contrast medium in their body and preferably while further contrast material is administered to the patient. Spectral CT data is normally acquired at at least two (possibly more) different radiation energies.

It should be noted in this regard that X-ray sources of CT scanners sometimes have an extensive wideband X-ray spectrum. It is necessary in this case to distinguish between the acceleration voltage of an X-ray source (in kV) and the average radiation energy (the most frequently emitted energy of the X-ray quanta in keV). The acceleration voltages typically lie in the region of less than 100 kV for the lower radiation energy and more than 100 kV for the higher radiation energy. From this there is yielded for example an average radiation energy which lies in the range between 33 keV and 65 keV for the lower radiation energy and in the range between 65 keV and 100 keV for the higher radiation energy.

In CT systems featuring two different tube voltages, an acceleration voltage between 70-100 kV is taken in practice for example for the lower radiation energy. The associated average radiation energy then typically lies approximately between 50 keV and 65 keV. An acceleration voltage between for example 120 kV and 140 kV is taken for the higher radiation energy. The associated average radiation energy then typically lies approximately between 70 keV and 80 keV.

A reconstruction of virtual monoenergetic images from the CT data which when combined result in a 3D image of at least a part of the patient (at a constant standard energy) is generally known in the prior art. However, a special aspect of one or more example embodiments is the variation in the VMI energy along the patient longitudinal axis. This variation should lie close to the real change in the contrast medium concentration in the patient. Preferably, this variation is monotonically decreasing in one direction, in particular toward the feet of the patient, i.e. in the craniocaudal direction.

An output of the virtual monoenergetic images can be a presentation on a display or the storing of the images. A forwarding of the image data for further calculations or for a postprocessing activity is also an output.

Even if the reconstruction can be conducted by a diagnostic assessment station, it is preferred that the complete method be performed by a CT system which acquires the data, reconstructs it and outputs it for further diagnostic assessment or for storing.

In practice, the method can be realized as follows: A CT system that has the capability to acquire spectral data, i.e. in particular a CT system featuring photon-counting detectors, but also a different CT system, such as for example a dual-source CT system, a CT system having a dual-layer detector, a CT system using kV switching or a CT system having split prefilters (TwinBeam), acquires the CT data at a default voltage (for example at 120 kV) at two or more average radiation energies. From the acquired data, virtual monoenergetic images are then reconstructed, the VMI energy of which varies along the patient longitudinal axis (in the z-direction) and which particularly preferably is fitted automatically to the respective iodine contrast at this position. During the reconstruction of a scan volume, this results in an image stack of virtual monoenergetic images acquired at energies varied in the z-direction. In this way, for example in the case of pulmonary CTAs in the shoulder region, VMIs are calculated at high VMI energy, and the VMI energy decreases rapidly, though preferably without an abrupt transition, along the z-axis in the craniocaudal direction (scan direction) to a desired default value, for example 55 keV. On the other hand, in the case of CTAs of the aorta and the pelvic or leg vessels, the VMI energy can decrease slowly along the z-axis in the direction of the legs from a predefined default value, for example 55 keV, for example to a value of 40 keV for example, in order to compensate for a decrease in contrast possibly caused by a non-optimized contrast medium protocol. In this case the VMI energy should not lie below the K-edge threshold of the contrast medium, which in the case of iodine for example amounts to 33 keV.

The device according to one or more example embodiments for reconstructing virtual monoenergetic images comprises the following components:

a data interface configured for receiving spectral CT data acquired at at least two different average radiation energies, a VMI unit configured for reconstructing virtual monoenergetic images from the CT data, the VMI energy of which images varies along the patient longitudinal axis and which together result in a 3D image of at least a part of the patient, a data interface configured for outputting the virtual monoenergetic images.

The mode of operation of the components has already been described within the scope of the method. The device is preferably configured for performing the method according to one or more example embodiments.

In particular, the features and advantages described in connection with the inventive method can also be embodied as corresponding subunits of the inventive device or of the inventive control facility, of the inventive computed tomography system and of the inventive computer program product.

Conversely, the features and advantages described in connection with the inventive device or the inventive control facility, the inventive computed tomography system and the inventive computer program product can also be embodied as corresponding method steps of the inventive method.

An inventive control facility for controlling a computed tomography system is configured for performing an inventive method and/or comprises an inventive device.

An inventive computed tomography system comprises an inventive control facility.

Most of the aforementioned components of the device can be realized wholly or partly in the form of software modules in a processor of a corresponding computing system, for example by a control facility of a computed tomography system. A largely software-based implementation has the advantage that computing systems already used previously in the prior art can also be easily upgraded via a software update in order to operate in the manner according to one or more example embodiments. In that respect the object is also achieved via a corresponding computer program product comprising a computer program which can be loaded directly into a computing system and has program sections for performing the steps of the inventive method, at least the steps that are executable via a computer, when the program is executed in the computing system. It should be said in this regard that the acquisition of spectral CT data in this implementation corresponds to a receiving of CT data, for example via a data bus or by readout from a memory unit. In addition to the computer program, such a computer program product may, where appropriate, comprise additional constituent parts, such as for example a set of documentation, and/or additional components, including hardware components, such as for example hardware keys (dongles, etc.), to enable use of the software.

A computer-readable medium, for example a memory stick, a hard disk drive or some other transportable or permanently installed data medium, on which the program sections of the computer program that can be read in and executed by a computing system are stored, can serve for transporting the computer program product to the computing system or to the control facility and/or for storing the same on or in the computing system or the control facility. For this purpose, the computing system can for example have one or more cooperating microprocessors or the like.

Further particularly advantageous embodiments and developments of the invention will become apparent from the dependent claims as well as from the following description, wherein the claims of one claims category may also be developed analogously to the claims and parts of the description relating to a different claims category and in particular also individual features of different exemplary embodiments or variants can be combined to form new exemplary embodiments or variants.

According to a preferred method, two different X-ray spectra are chosen for the acquisition of spectral CT data at at least two different radiation energies. The one (low-energy) X-ray spectrum preferably results from an acceleration voltage of max. 100 kV. It has in particular an average radiation energy between 33 keV and 65 keV. The other (high-energy) X-ray spectrum preferably results from an acceleration voltage of more than 100 kV. It has in particular an average radiation energy between 65 keV and 100 keV.

If a CT system comprising a wideband source and one or more detectors is available, it is preferred that energy-selective detectors acquire the data at a low average radiation energy in the range between 33 keV and 70 keV and at a higher average radiation energy in the range 55 keV to 100 keV.

According to a preferred method, a CT system featuring photon-counting detectors, a dual-source CT system, a CT system having a dual-layer detector, a CT system using kV switching or a CT system having split prefilters is used for the acquisition of spectral CT data.

According to a preferred method, the contrast medium concentrations prevailing at a number of positions along the longitudinal axis of a patient are determined for said positions.

The contrast medium concentrations can be determined in particular via measurements (for example CT images) and/or via interpolations between known values. For example, the contrast medium concentrations can be measured point by point at different positions on the patient longitudinal axis and the contrast medium concentrations at points lying therebetween can be interpolated, for example by fitting a curve to the measurement points according to an Nth-order polynomial.

During the reconstruction of the virtual monoenergetic images from positions along the longitudinal axis of the patient, the VMI energy of said images is then automatically fitted to the iodine concentrations determined for these positions. This can be done according to a table or according to a mathematical function. For example, in the case in which the iodine concentration in the z-direction corresponds to a curve of the function $f(z)$, the progression of the VMI energy could behave according to the function $a \cdot f(x)$ with the constant factor a. It is however preferred to obtain a calibration curve for the VMI energy from test measurements. This is explained in greater detail hereinbelow.

It is also preferred that a measure for the contrast medium concentrations (for example iodine concentrations) prevailing in a reference vessel or reference tissue be determined for a number of positions along the longitudinal axis of a patient from CT values of virtual monoenergetic test images acquired at a fixed energy or from spectral contrast medium images (for example iodine images). In the then following reconstruction of the virtual monoenergetic images, their VMI energy from positions along the longitudinal axis of the patient is then automatically fitted to the measure determined for these positions for the respective contrast medium concentration (for example iodine concentration), thus resulting in a desired progression of the CT values along the patient longitudinal axis.

According to a preferred method, the automatic specification of the respective VMI energy for reconstructing the virtual monoenergetic images of a patient is conducted according to the following steps:

- reconstructing an image dataset of virtual monoenergetic images acquired at a predefined default energy,
- (automatically) segmenting a number of reference vessels of the reconstructed image dataset, in particular the subclavian vein and/or the superior vena cava and/or the aorta,
- (automatically) measuring average CT values in a predefined region (ROI: Region of Interest) of the segmented number of reference vessels for the positions of the virtual monoenergetic images, preferably in HU (Hounsfield Units),
- determining a progression of the measured CT values along the longitudinal axis of the patient and calculating the VMI energies according to said progression,
- reconstructing a new image dataset of virtual monoenergetic images at the calculated VMI energies according to the progression of the measured CT values, in particular in such a way that a desired progression is produced via virtual monoenergetic images at the calculated energies.

When an image dataset of virtual monoenergetic images is reconstructed for the first time, a default energy is predefined. This is a VMI energy which is specified in advance and which does not vary. In this regard it is possible to be guided by the prior art. One of the VMI energies chosen there can be predefined as the default energy.

An (automatic) segmentation of a number of reference vessels of the reconstructed image dataset is known in the prior art. This can happen using "normal" algorithms or using learning-capable models trained via machine learning. Such algorithms or models are known in the prior art and in particular are suitable for detecting the subclavian vein and/or the superior vena cava and/or the aorta in the images and segmenting them there.

Likewise known in the prior art is the (automated) measurement of an average CT value in a predefined region of the segmented number of reference vessels for the positions of the virtual monoenergetic images. CT values are usually specified in Hounsfield units (HU).

According to one or more example embodiments, the progression of the measured CT values along the longitudinal axis of the patient can now be determined from the measured values, for example by plotting the measured values at their positions on the longitudinal axis and by fitting a curve (for example an Nth-order polynomial). The VMI energies can then be calculated in accordance with this progression.

In practice, the CT values of an iodine sample could be determined in advance in a phantom in VMIs acquired at a plurality of energies from 40 keV to 190 keV for example. A phantom could have an abdomen-like cross-section. The iodine sample could be a syringe filled with iodine of a specific concentration. If the CT values are plotted as a function of the energy of the VMIs, a calibration curve is produced therefrom with the aid of which the corresponding target energy of the VMIs can then be derived from the CT values measured at the different positions in the patient.

Using the calculated VMI energies, it is now possible to reconstruct a new image dataset of virtual monoenergetic images according to the inventive method. An image at a longitudinal axis position is reconstructed via the VMI energies calculated there.

The automatic specification of the VMI energy in each slice can therefore be performed for example in such a way that initially an image dataset of VMIs acquired at a specified energy is calculated. In this image dataset, an automatic segmentation of reference vessels (in pulmonary CTAs, for example subclavian vein, superior vena cava; in abdomen/pelvis CTAs, the aorta) is performed in which in each slice in an automatically specified ROI the average CT value is measured in HU. From the progression of the CT values in the z-direction there results a progression curve of the VMI energies of the VMIs in the z-direction. A new image dataset of VMIs is thereupon calculated in which each VMI has the VMI energy desired at the respective z-position.

According to a preferred method, virtual monoenergetic images acquired at variable VMI energies in the craniocaudal direction are generated during the reconstruction. It is preferred in this case that the respective VMI energy of the virtual monoenergetic images decreases in the craniocaudal direction, in particular strictly monotonically.

According to a preferred method, an image stack of virtual monoenergetic slice images is generated during the reconstruction of the VMIs. It is preferred in this case that the slice images of the image stack lie parallel to the transverse plane or parallel to the sagittal plane. Of course, these images must not necessarily be aligned along the z-axis, even if this represents an advantageous embodiment variant.

According to a preferred method, a virtual monoenergetic image acquired at a first VMI energy is reconstructed in the course of a pulmonary CTA in the shoulder region of a patient. The respective VMI energy during the reconstruction of further virtual monoenergetic images then decreases along the longitudinal axis of the patient in the craniocaudal direction. It is preferred in this case that the progression of the VMI energies exhibits no abrupt transition, i.e. the progression is constant and in particular also differentiable. It is preferred that the VMI energy decreases down to a value between 40 keV and 60 keV.

According to a preferred method, during a CTA scan of the aorta and/or the pelvic or leg vessels of a patient, the VMI energies of the virtual monoenergetic images decrease continuously along the longitudinal axis of the patient in the direction of the legs from a first value, in particular between 50 keV and 80 keV, in particular to a VMI energy between 40 keV and 50 keV.

The use of AI-based methods (AI: Artificial Intelligence) is preferred for the method according to one or more example embodiments, in particular for the segmentation of vessels and/or for determining VMI energies from contrast medium concentrations. An artificial intelligence application is based on the principle of machine-based learning and is generally performed via a suitably trained algorithm that is capable of learning. The term “machine learning” is often used for machine-based learning, the principle of “deep learning” also being incorporated in this concept.

Components of one or more example embodiments, in particular components for reconstructing VMIs, are preferably present in the form of a “cloud service”. Such a cloud service serves for processing data, in particular via an artificial intelligence app, but may also be a service based on conventional algorithms. Generally, a cloud service (also referred to below as “cloud” for short) is an IT infrastructure in which for example storage space or computing power and/or application software is made available via a network. In this case communication between the user and the cloud is accomplished via data interfaces and/or data transmission protocols. In the present case it is particularly preferred that the cloud service provides both computing power and application software.

Within the scope of a preferred method, data is provided to the cloud service via the network. The cloud service comprises a computing system, for example a computer cluster, which usually does not include the local computer of the user. Said cloud can be provided in particular by the medical facility that also provides the medical engineering systems. For example, the data of an image acquisition is sent to a (remote) computer system (the cloud). Preferably, the computing system of the cloud, the network and the medical engineering system constitute a cluster in the information technology sense. The method can in this case be realized via a command constellation in the network. The data calculated in the cloud (“result data”) is subsequently sent via the network again to the local computer of the user.

FIG. 1 shows an embodiment of a computed tomography system (CT system) 1 comprising a radiation detector 4 and a radiation source 5. The radiation source 5 is embodied to expose the radiation detector 4 to radiation. The CT system 1 shown comprises a gantry 2 having a rotor 3. The rotor 3 comprises an X-ray source as radiation source 5 and the radiation detector 4, which is embodied to detect X-rays.

The radiation detector 4 and/or the radiation source 5 are configured for acquiring spectral CT data. Thus, the radiation source 5 can be wideband for example and the radiation detector 4 can detect two or more energies in a resolved manner. However, the radiation source 5 may also successively emit the two or more different spectra, which are then detected by the radiation detector 4. It is also possible that the gantry 2 comprises two or more systems composed of radiation source 5 and radiation detector 4, which measure in different energy spectra.

The rotor 3 is rotatable around the axis of rotation 8, which in this case can simultaneously be regarded as the patient longitudinal axis 8. The patient 6 is positioned on the patient couch 7 and can be moved through the gantry 2 along the axis of rotation 8. The computing unit 9 is provided for controlling the imaging system 1 and/or for generating an image dataset based on the signals detected by the radiation detector 4.

Typically, a (raw) X-ray image dataset of the object 6 is acquired via the radiation detector 4 from a plurality of angular directions at a radiation energy in each case, i.e. two or more raw datasets. Subsequently, a final image dataset can be reconstructed based on the (raw) X-ray image dataset via a mathematical method, for example comprising a filtered backprojection or an iterative reconstruction method. In this case the image dataset comprises virtual monoenergetic images B which have been reconstructed via the method according to one or more example embodiments.

The computing unit 9 can comprise or be a control facility 9 for controlling the CT system 1 and a generation unit for generating an X-ray image dataset. In the case presented here, the computing unit 9 is the control facility 9.

In addition, an input facility 10 and an output facility 11 are connected to the computing unit 9. The input facility 10 and the output facility 11 can for example facilitate an interaction by a user or enable the visualization of a generated image dataset or output a determined problem solution.

Figure 3:
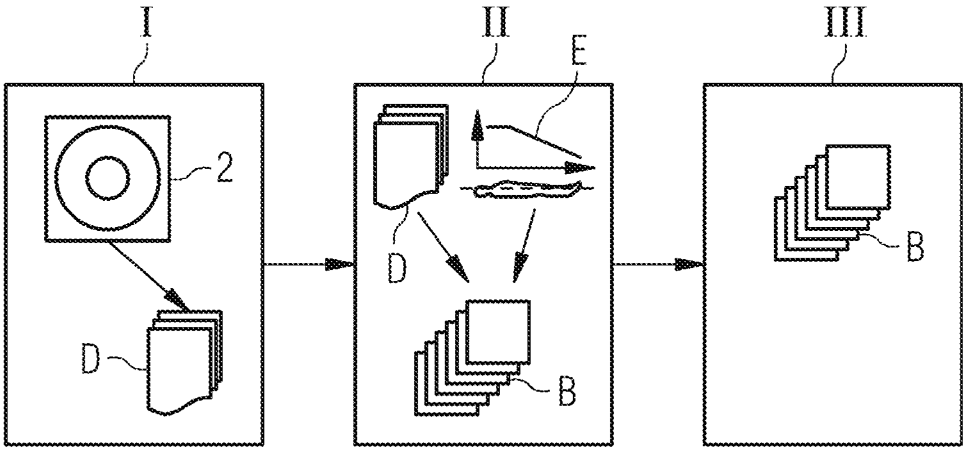
FIG. 3 shows an outline illustrating a method workflow sequence according to one or more example embodiments.

The computing unit 9 as control facility 9 in this case comprises a device 14 for reconstructing virtual monoenergetic images B according to one or more example embodiments (see for example FIG. 3). Said device 14 comprises a data interface 12 and a VMI unit 13.

The data interface 12 is configured for receiving spectral CT data D acquired at at least two different average radiation energies as well as for outputting the virtual monoenergetic images B.

The VMI unit 13 is configured for reconstructing virtual monoenergetic images B from the CT data D, which together result in a 3D image of at least a part of the patient 6. The VMI energy E of said VMIs B in this case varies along the patient longitudinal axis 8.

The CT system illustrated here can be for example a CT system 1 comprising photon-counting detectors, a dual-source CT system 1, a CT system 1 featuring a dual-layer detector, a CT system 1 using kV switching or a CT system 1 having split prefilters.

The following figures show how the reconstruction of the VMIs B is performed.

Figure 2:
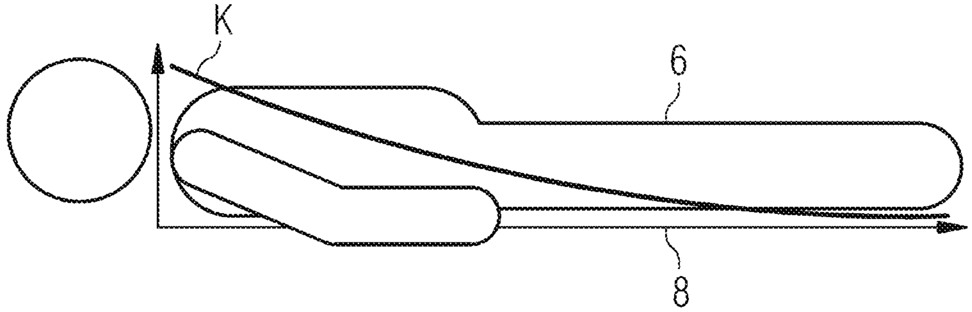
FIG. 2 shows an outline illustrating the progression of a contrast medium concentration in a human body according to one or more example embodiments.

FIG. 2 shows an outline illustrating the progression of a contrast medium concentration K in a human body. In the background there is shown the silhouette of a patient 6, to whom a contrast medium has been applied in the upper part of the body. The contrast medium concentration K decreases toward the feet, i.e. in the craniocaudal direction, as the curve shows.

FIG. 3 shows an outline illustrating the workflow sequence of a method for reconstructing virtual monoenergetic images B in the form of a block diagram.

In step I, spectral CT data D is acquired at at least two different average radiation energies. It can be assumed that the acquisition was performed using a CT system according to FIG. 1, spectral CT data D having been acquired at at least two different average radiation energies. For this purpose, for example two different X-ray spectra could be chosen, preferably one resulting from an acceleration voltage of max. 100 kV and in particular an average radiation energy between 33 keV and 65 keV, and one resulting from an acceleration voltage of more than 100 kV and in particular an average radiation energy between 65 keV and 100 keV. However, an energy-selective radiation detector 4 may also be present which is able to record the data at a low average radiation energy in the range between 33 keV and 70 keV and a higher average radiation energy in the range 55 keV to 100 keV.

In step II, virtual monoenergetic images B are reconstructed from the CT data D and a progression curve for the VMI energy E such that the VMI energy E of the VMIs B varies along the patient longitudinal axis 8. Taken together, these VMIs B produce a 3D image of at least a part of the patient 6.

For this purpose it is possible, for example for a number of positions along the longitudinal axis 8 of a patient 6, to determine the contrast medium concentrations K prevailing there, and during the reconstruction of the virtual monoenergetic images B of positions along the longitudinal axis 8 of the patient 6, the VMI energy E can be automatically fitted to the contrast medium concentrations K determined for these positions. This is shown schematically in FIGS. 2 and 4.

An output of the virtual monoenergetic images B takes place in step III.

Figure 4:
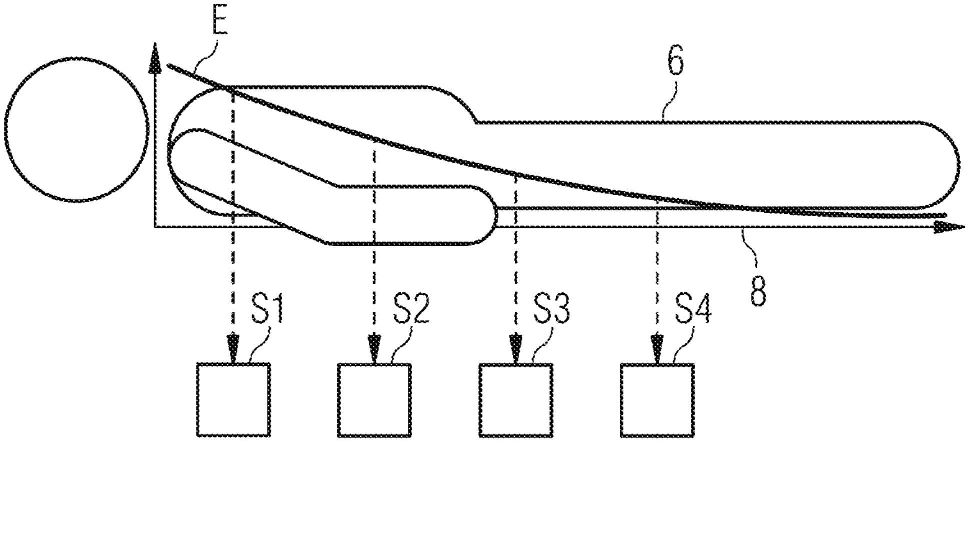
FIG. 4 shows a VMI image stack with a curve illustrating the decline in VMI energy according to one or more example embodiments.

FIG. 4 shows a VMI image stack S comprising a total of four slice images S1, S2, S3, S4 along with a curve illustrating the decline in the VMI energy E during a progression of the contrast medium concentration K according to FIG. 2. This figure is similar to FIG. 2, with the difference that in this case the VMI energy E is plotted, not the contrast medium concentration K. Slice images S1, S2, S3, S4 are reconstructed at different positions on the longitudinal axis 8 of the patient based on the VMI energies E present there.

It can be assumed that the VMI energies at the relevant points were determined via measurements and the illustrated progression curve was interpolated for further slice images between these points.

In conclusion, it is pointed out once again that the figures described in detail in the foregoing are simply exemplary embodiments which may be modified in the most diverse ways by the person skilled in the art without leaving the scope of the invention. Furthermore, the use of the indefinite articles "a" or "an" does not exclude the possibility that the features in question may also be present more than once. Similarly, the terms "unit" and "device" do not rule out the possibility that the components in question may consist of a plurality of cooperating subcomponents, which if necessary may also be distributed in space. The expression "a number" is to be understood as "at least one". Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including “on,” “connected,” “engaged,” “interfaced,” and “coupled.” Unless explicitly described as being “direct,” when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being “directly” on, connected, engaged, interfaced, or coupled to another element, there are no intervening elements present. Other words used to describe the relationship between elements should be interpreted in a like fashion (e.g., “between,” versus “directly between,” “adjacent,” versus “directly adjacent,” etc.).

The terminology used herein is for the purpose of describing particular embodiments only and is not intended to be limiting of example embodiments. As used herein, the singular forms “a,” “an,” and “the,” are intended to include the plural forms as well, unless the context clearly indicates otherwise. As used herein, the terms “and/or” and “at least one of” include any and all combinations of one or more of the associated listed items. It will be further understood that the terms “comprises,” “comprising,” “includes,” and/or “including,” when used herein, specify the presence of stated features, integers, steps, operations, elements, and/or components, but do not preclude the presence or addition of one or more other features, integers, steps, operations, elements, components, and/or groups thereof. As used herein, the term “and/or” includes any and all combinations of one or more of the associated listed items. Expressions such as “at least one of,” when preceding a list of elements, modify the entire list of elements and do not modify the individual elements of the list. Also, the term “example” is intended to refer to an example or illustration.

It should d also be noted that in some alternative implementations, the functions/acts noted may occur out of the order noted in the figures. For example, two figures shown in succession may in fact be executed substantially concurrently or may sometimes be executed the order, in reverse depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed parallel, in concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as “processing” or “computing” or “calculating” or “determining” of “displaying” or the like, refer to the action and processes of a computer system, or similar electronic computing device/hardware, that manipulates and transforms data represented as physical, electronic quantities within the computer system’s registers and memories into other data similarly represented as physical quantities within the computer system memories or registers or other such information storage, transmission or display devices.

In this application, including the definitions below, the term ‘module’ or the term ‘controller’ may be replaced with the term ‘circuit.’ The term ‘module’ may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A method for reconstructing virtual monoenergetic images, the method comprising:

acquiring spectral CT angiography data at at least two different average radiation energies;

reconstructing virtual monoenergetic images (VMIs) from the CT angiography data, a first VMI being reconstructed at a first VMI energy and respective VMI energies of further VMIs decrease along a longitudinal axis of a patient in a craniocaudal direction, a 3D image of at least a part of the patient being based on the VMIs; and outputting the virtual monoenergetic images.

2. The method of claim 1, wherein the acquiring includes:

selecting two different X-ray spectra; and acquiring, by an energy-selective radiation detector, the spectral CT angiography data at a first average radiation energy between 33 keV and 70 keV and a second average radiation energy range between 55 keV to 100 keV.

3. The method of claim 2, wherein one X-ray spectra results from an average radiation energy between 33 keV and 65 keV, and another X-ray spectra results from an average radiation energy between 65 keV and 100 keV.

4. The method of claim 1, wherein the acquiring acquires the spectral CT angiography data using a CT system including photon-counting detectors, a dual-source CT system, a CT system having a dual-layer detector, a CT system using kV switching or a CT system having split prefilters.

5. The method of claim 1, wherein the reconstructing includes:

determining contrast medium concentrations for a number of positions along the longitudinal axis of a patient; and fitting the respective VMI energy of said images to the contrast medium concentrations.

6. The method of claim 5, wherein a specification of the respective VMI energy for reconstructing the virtual monoenergetic images of a patient is performed according to:

reconstructing an image dataset of virtual monoenergetic images acquired at a predefined default energy;

segmenting a number of reference vessels of the reconstructed image dataset;

measuring average CT values in a predefined region of the segmented number of reference vessels for positions of the virtual monoenergetic images;

determining a progression of measured CT values along the longitudinal axis of the patient and calculating the VMI energies according to the progression; and reconstructing a new image dataset of virtual monoenergetic images acquired at the calculated VMI energies according to the progression.

7. The method of claim 6, wherein the reference vessels include at least one of a subclavian vein, a superior vena cava, or an aorta.

8. The method of claim 5, wherein the contrast medium concentrations are determined via at least one of measurements or interpolations between known values.

9. The method of claim 1, wherein the reconstructing includes:

generating an image stack of virtual monoenergetic slice images is generated during the reconstruction of the virtual monoenergetic images.

10. The method of claim 9, wherein the slice images of the image stack lie parallel to a transverse plane or parallel to a sagittal plane.

11. A non-transitory computer-readable storage medium comprising commands which, when executed by a computer, cause the computer to perform the method of claim 1.

12. A device for reconstructing virtual monoenergetic images comprising:

a data interface configured to receive spectral CT angiography data acquired at at least two different average radiation energies;

a virtual monoenergetic image (VMI) unit configured to reconstruct virtual monoenergetic images (VMIs) from the CT angiography data, the VMI unit configured to reconstruct a first VMI at a first VMI energy and reconstruct further VMIs at respective VMI energies that decrease along a longitudinal axis of a patient in a craniocaudal direction, a 3D image of at least a part of the patient being based on the VMIs; and a data interface configured to output the virtual monoenergetic images.

13. A control facility configured to control a computed tomography system comprising the device of claim 12.

14. A computed tomography system comprising the control facility of claim 13.

* * * * *